United States Patent

Hoskin et al.

[11] Patent Number: 5,879,368
[45] Date of Patent: *Mar. 9, 1999

[54] GAS-TIGHT SEAL FOR SURGICAL TROCARS

[75] Inventors: William John Hoskin, deceased, late of Harpenden, United Kingdom, by Elizabeth Anne Newell, legal representative; Nicholas Richard Kemp, Luton, United Kingdom

[73] Assignee: 3i Group plc, London, United Kingdom

[ * ] Notice: The term of this patent shall not extend beyond the expiration date of Pat. No. 5,730,728.

[21] Appl. No.: 926,092

[22] Filed: Sep. 9, 1997

Related U.S. Application Data

[63] Continuation of Ser. No. 704,765, Sep. 26, 1996, Pat. No. 5,730,728 which is a continuation of PCT/GB95/00645 Mar. 23, 1995.

[30] Foreign Application Priority Data

Mar. 26, 1994 [GB] United Kingdom .................... 9406038
Oct. 13, 1994 [GB] United Kingdom .................... 9420633

[51] Int. Cl.⁶ ...................................................... A61M 3/00
[52] U.S. Cl. ........................................... 606/185; 604/167
[58] Field of Search .............................. 606/1, 184, 185; 604/164–167, 264

[56] References Cited

U.S. PATENT DOCUMENTS

| | | |
|---|---|---|
| 5,176,652 | 1/1993 | Littrell ..................................... 604/167 |
| 5,201,714 | 4/1993 | Gentelia et al. . |
| 5,342,315 | 8/1994 | Rowe et al. . |
| 5,380,288 | 1/1995 | Hart et al. ................................ 606/185 |
| 5,397,335 | 3/1995 | Gresl et al. ............................. 606/185 |
| 5,476,475 | 12/1995 | Gadberry ................................ 606/185 |
| 5,496,280 | 3/1996 | Vandenbroek et al. ................. 604/167 |

FOREIGN PATENT DOCUMENTS

| | | |
|---|---|---|
| 0542432A1 | 5/1993 | European Pat. Off. . |
| WO9301850 | 2/1993 | WIPO . |
| WO9304717 | 3/1993 | WIPO . |
| WO9417844 | 8/1994 | WIPO . |

*Primary Examiner*—William Lewis
*Attorney, Agent, or Firm*—Christie, Parker & Hale, LLP

[57] ABSTRACT

A gas-tight seal module is incorporated in a trocar system to form a gas-tight seal about an instrument inserted into the cannula of the trocar system. The module incorporates an apertured disc. The aperture in the disc can be stretched to accommodate a seal about an instrument inserted into the cannula. The disc is carried by a flaccid membrane which extends across the module. A pair of rigid washers clamped on opposite sides of the disc are constrained for movement between two parallel spaced surfaces. The disc is thus freely moveable in its own plane to accommodate off-axis movement of the instrument thus avoiding the breakage of the seal with the instrument which would otherwise occur if the disc did not have the same freedom of movement. The disc also acts to clean the surface of the instrument when withdrawn so as to avoid contamination of a flap valve upstream of the disc.

10 Claims, 2 Drawing Sheets

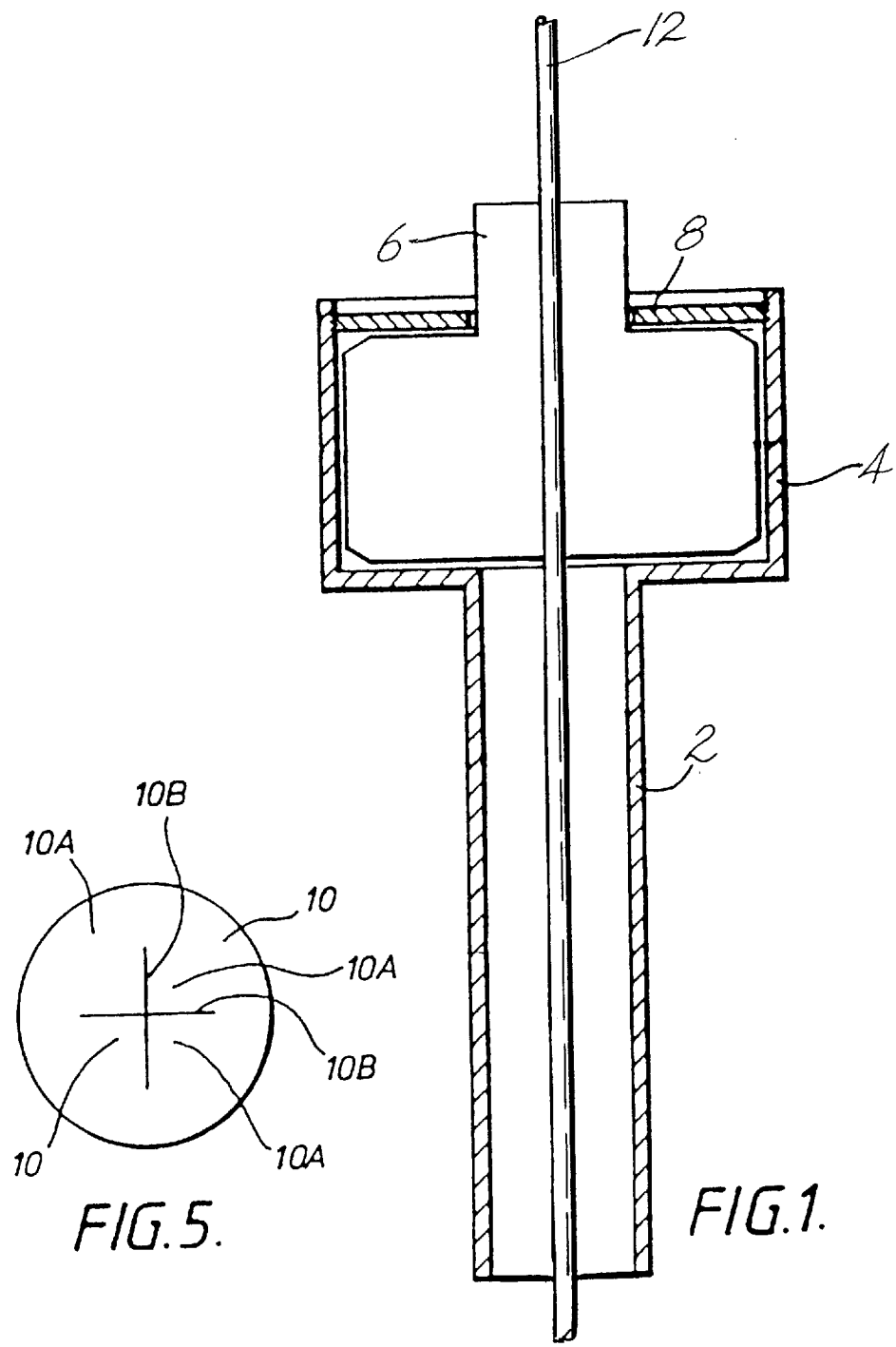

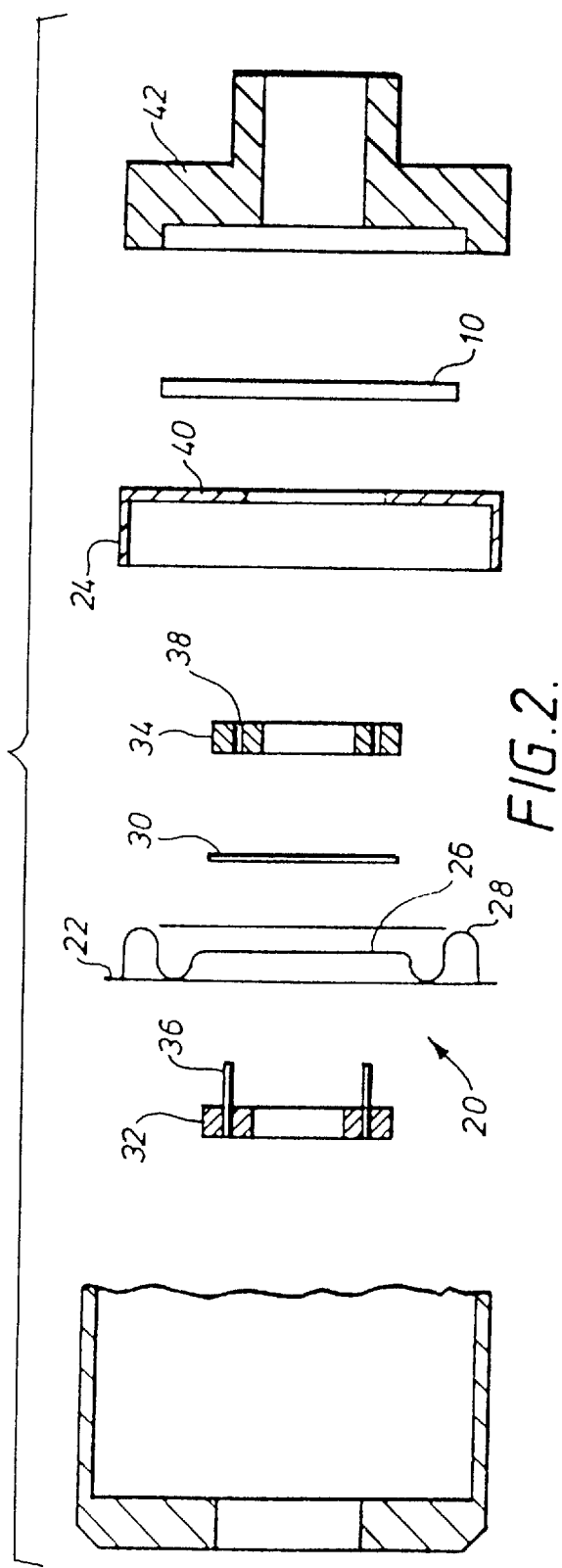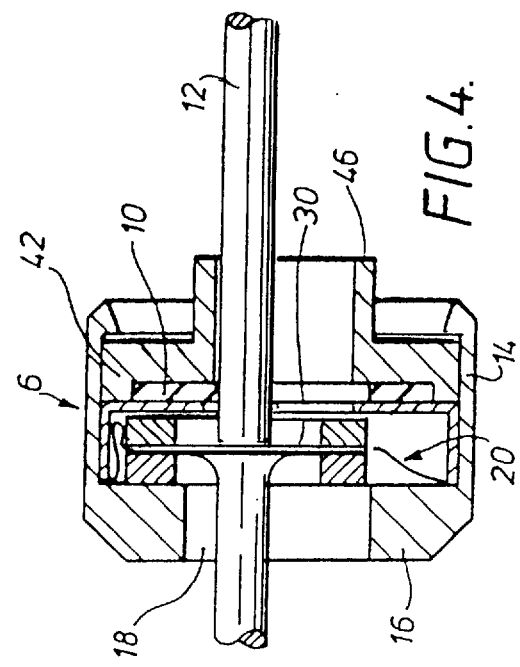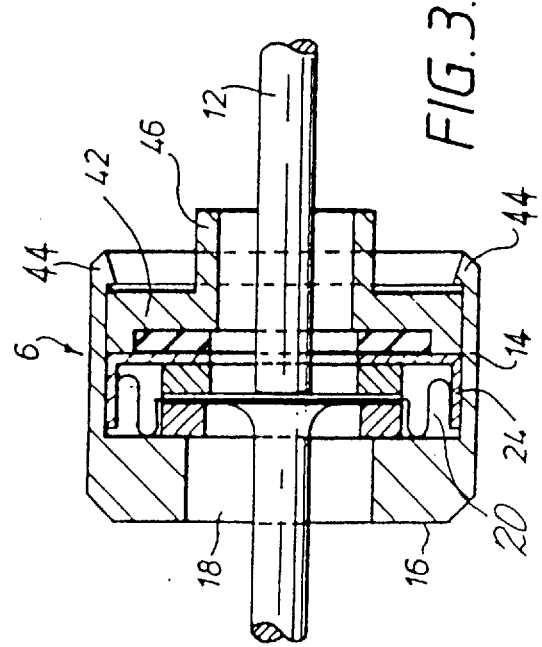

5,879,368

GAS-TIGHT SEAL FOR SURGICAL TROCARS

CROSS-REFERENCE TO RELATED APPLICATION

This is a continuation of patent application Ser. No. 08/704,765 filed Sept. 26, 1996, U.S. Pat. No. 5,730,728 which is the U.S. national-stage filing of PCT International Application No. PCT/GB95/00645 filed Mar. 23, 1995, which claimed priority of U.K. Application No. 9406038.1 filed Mar. 26,1994 and U.K. Application No. 9420633.1 filed Oct. 13, 1994.

BACKGROUND OF THE INVENTION

The present invention relates to gas-tight seals and to trocar systems incorporating such seals.

Trocar systems are used during abdominal operations for maintaining a passage through the abdominal wall of a patient. Trocar systems generally comprise a cannula in the form of an elongate tube terminating in an enlarged upper body and an obturator or cutting tool which is fed through the enlarged upper body and down the elongate tube to pierce the abdominal wall so that the elongate tube can follow the tool through the wall. The cutting tool is then removed leaving the way clear for elongate surgical instruments or equipment, such as endoscopes, to be fed into the abdomen through the tube. To provide space within the abdomen, the abdomen is inflated with a gas and this allows easy access to the various organs located within the abdomen. To maintain gas pressure the trocar system is provided with a flap valve which is urged by the pressure of gas into a closed state. The flap valve must, however, be opened to allow the passage of surgical tools. Accordingly a sealing system is provided in the enlarged upper body to provide a seal around the surgical instrument once it has been inserted into the enlarged upper body. This now creates a gas lock between the flap valve and the seal and so the flap valve can now be opened (either by pushing the instrument against it or by other means) substantially without loss of pressure in the abdomen. The instrument can now be fed into the abdomen and manipulated as required. Usually more than one trocar is used so as to provide multiple entry points into the abdomen.

The diameter of the instruments used is usually much smaller than the diameter of the tube or the enlarged body and so a considerable amount of lateral off-axis movement of the instruments can and does take place in order to effect the desired manipulation of the instrument. Because the seals used are static, any movement of the instrument other than axial can to strain the seal to the extent of temporarily breaking the seal and so allowing gas to escape. Also most seals are designed with a specific diameter of instrument in mind and so different seals or adaptors are required when changing instruments.

It is an object of the invention to provide an improved seal.

SUMMARY OF THE INVENTION

According to the present invention there is provided a trocar comprising an elongate tail portion for insertion through the abdominal wall of a patient and a head portion defining a compartment accommodating a replaceable seal module, the seal module comprising a housing containing a gas impermeable barrier extending across a chamber in said housing and secured to make a substantially gas-tight seal with the internal wall of the chamber, said barrier having a central elastic portion with an opening which can be stretched to accommodate the passage of elongate instruments of different cross section to form a substantially gas-tight seal with such instruments, means for constraining said central portion which allows displacement, relative to the compartment in a predetermined plane, substantially without impediment.

According to the present invention there is further provided a replaceable seal module for a trocar comprising a housing defining a chamber, a barrier extending across said chamber to make a substantially gas-tight seal with the internal wall of the chamber, the barrier having a generally central elastic portion with an opening which can be stretched to accommodate the passage of elongate instruments of different cross sections to form a substantially gas tight seal with such instruments, means for constraining the central portion for displacement in a plane substantially perpendicular to the axis of the opening, the outer portion of the barrier allowing displacement of the central portion substantially without resistance.

BRIEF DESCRIPTION OF THE DRAWINGS

A gas-tight seal embodying the present invention will now be described, by way of example with reference to the accompanying diagrammatic drawings in which:

FIG. 1 is a section of a trocar system through which a surgical instrument has been passed;

FIG. 2 is a fragmentary exploded view of the gas-tight seal module of the trocar system;

FIG. 3 is a section through the gas-tight seal module accommodating a surgical instrument;

FIG. 4 is the same section as in FIG. 3 but with the surgical instrument laterally displaced; and FIG. 5 is a plan view of a valve seal used in the module of FIG. 2.

DETAILED DESCRIPTION

The trocar system shown in FIG. 1 comprises an elongate tube or tail 2 terminating in an enlarged head or upper body portion 4. The enlarged upper body portion 4 has a compartment which accommodates a removable seal module 6. The seal module 6 may be sealingly locked into the body portion 4 by a screw threaded cap 8. An elongate medical instrument 12 (for example, the optical probe of an endoscope) passes through the seal module 6 and the tube 2.

The seal module 6 is shown in more detail in FIG. 3. The module 6 comprises a cylindrical body portion 14 defining a chamber which is open at one axial end and closed by an end wall 16 at the opposite axial end. The end wall 16 has a central circular opening 18. A barrier in the form of a membrane 20 extends across the inner chamber defined by the body portion 14. The membrane 20 has a flat outer circumferential portion 22 (see FIG. 2) having an outer circumference substantially equal to the inner circumference of the body portion 14. A cylindrical clamping ring 24 is located within the chamber to urge the circumferential portion 22 against the inner face of the end wall 16.

The membrane 20 has a central disc shaped portion 28 and an intermediate undulating portion 28 which allows the central disc-shaped portion 26 to move freely within predetermined limits with respect to the outer circumferential portion. The membrane is of flaccid material, for example latex. The central disc shaped portion 28 is reinforced with a disc 30 of silicone material. The disc 30 is clamped to the disc shaped portion 28 with the aid of a pair of cooperating rigid washers 32 and 34. Pins 36 in the washer 32 pass through mating holes in the disc 30 and portion 26 to engage in a locking (push-fit) manner with corresponding holes 38 in the washer 34.

The clamping ring 24 has a radially inwardly extending flange 40 which when the ring 24 clamps the portion 22 against the wall 16 forms with the wall 16 a space in which the subassembly of washers 32 and 34 has just sufficient clearance for sliding movement in the plane of the disc 30. The central portion 26 and the disc 30 are thus imprisoned or constrained for movement in two dimensions in their own planes.

A locking member 42 is accommodated in the body portion 14 to urge the clamping ring into clamping engagement with the outer circumferential portion 22. The locking member 42 may be a push fit under a circumferential lip 44 at the open axial end of the body portion to lock the components of the module 6 together. If a modification is desired other methods of locking the locking member in place may be used for example by using a circle clip engaging a groove on the inner face of the body portion 14 or by means of a screw thread on the locking member engaging a corresponding screw thread on the inner face of the body portion 14. The locking member has an annular collar 46. The internal diameter of the locking member 42 and the washers 32 and 34 are substantially equal to the diameter of the opening 18.

The silicone disc 30 and the disc shaped portion 26 each have an aperture therein substantially smaller than the opening 18. For example the aperture may have a diameter, when the disc is unstressed, of less than a quarter of the diameter of the opening 18.

The diameter of the aperture in the disc, when unstressed, should also be smaller than the diameter of the smallest instrument that is intended to be used with the seal.

Because the disc is of silicone rubber the aperture can be stretched significantly beyond its original size by the insertion of larger diameter instruments. For example the diameter of the aperture could be more than doubled so as to accommodate different instruments having a diameter in the range of from 4 to 13 mm. The locking member 42 has a circular recess which accommodates an elastic circular disc 10 of silicone rubber. The disc is imprisoned between the locking member 42 and the clamping ring 24 but allowed a very slight amount of play so that it can readily resume its original shape when released from being stressed. The disc 10 has a pair of centrally intersecting slits 10B (see FIG. 5) which form four flaps 10A in the disc 10 which can be displaced by the pressure of the instrument 12. Normally the flaps 10A are closed and so therefore, they provide a valve which acts to prevent the escape of gas from the module. Instead of intersecting slits a single profiled cut can be made in the disc to form a displaceable flap for the instrument to displace and pass through. During operation the module 6 is locked into the enlarged upper portion of the body portion 4 of the trocar system using the cap 8. Upon the insertion of the instrument 12 the flaps 10A are displaced to allow the passage of the instrument 12 but will form a partial seal around the instrument 12. The instrument is then passed through the silicone disc 30 which will form a tight seal about the instrument. Upon withdrawal of the instrument 12 any debris drawn by the instrument from the abdominal area will be scraped off the instrument by the silicone disc 30 and so there is little or no danger of such debris being lodged in the slits of the disc 10 to prevent complete closure of the flaps upon withdrawal of the instrument. The complete closure of the flaps thus again prevents the escape of gas from the module.

The instrument 12 can be displaced radially of the module 6 substantially without resistance because of the flaccid undulating portion 28 (see FIG. 4). The disc 30 is, however, constrained against angular displacement out of its plane by the washers 32 and 34.

Instead of washers 32 and 34 being used to constrain the disc 30, axially extending projections on the axial end wall 16 and the flange 40 may be used to constrain the disc 30 for movement in its own plane. In this case the disc 30 may be welded or adhesively secured to the membrane 20. In yet another modification, the disc 30 may form an integral part of a composite membrane 20.

It will be appreciated that the module 6 can be manufactured as a disposable module to be discarded after a single use.

If the module is required to be reusable it can readily be removed from the trocar and autoclaved. Instead the module can be subject to gamma or ethylene-oxide LND treatment.

We claim:

1. A trocar comprising
an elongate tail portion for insertion through the abdominal wall of a patient,
a replaceable seal module and
a capped head portion defining a compartment for accommodating said replaceable seal module,
the cap of the head portion being movable between one state in which it opens the compartment to allow the seal module therein to be removed and replaced and another state in which it closes the compartment and secures the module therein, the seal module comprising
a housing defining a chamber having an internal wall,
a gas impermeable barrier extending across the chamber in said housing and secured to make a substantially gas-tight seal with the internal wall of the chamber, said barrier having
a central elastic portion with a stretchable opening for accommodating passage of elongate instruments of different cross-section to form a substantially gas-tight seal with such instruments.

2. A trocar according to claim 1 wherein an outer portion of said gas impermeable barrier is of latex.

3. A trocar according to claim 2 wherein said central elastic portion is of silicone rubber.

4. A trocar according to claim 1 wherein said housing is generally cylindrical, open at one axial end and closed at the opposite axial end except for a central opening substantially similar in size to said central portion, an annular clamping ring sized to be accommodated in said housing to urge the peripheral portion of said barrier against the closed axial end of the housing, a radially inwardly directed flange extending from said clamping ring and terminating in a central opening aligned with and having a size comparable with that of the central opening in said one axial end of said housing and a locking member for locking the clamping ring in the housing.

5. A seal according to claim 4 wherein said locking member forms a snap fit with said housing.

6. A seal according to claim 4 wherein said locking member includes an annular collar for guiding said elongate instruments towards the opening in said barrier.

7. A replaceable seal module for insertion into and removal from a compartment in a trocar, the module comprising a housing to be accommodated within the compartment and defining a chamber having an internal wall, a barrier extending across said chamber to make a substantially gas tight seal with-the internal wall of the chamber, the barrier having a generally central elastic portion with an opening which can be stretched for accommodating the passage of elongate instruments of different cross-section to form a substantially gas tight seal with such instruments.

8. A module according to claim 7 wherein the barrier extends across said chamber at a downstream end portion thereof and including a valve supported to extend across the chamber at an upstream end portion thereof, said valve being normally closed to prevent the escape of gas from said downstream end portion, but being openable to allow the passage of a said instrument therethrough.

9. A module according to claim 8 wherein said valve comprises a laminar member of resilient material provided with a cut defining at least one flap which can be displaced by the passage of said instrument.

10. A module according to claim 9 wherein said laminar member is provided with intersecting cuts which define a plurality of flaps.

* * * * *

UNITED STATES PATENT AND TRADEMARK OFFICE
CERTIFICATE OF CORRECTION

PATENT NO. : 5,879,368
DATED : March 9, 1999
INVENTOR(S) : William John Hoskin; Nicholas Richard Kemp It is certified that error appears in the above-identified patent and that said Letters Patent is hereby corrected as shown below:

Column 4, line 22, replace "ethylene-oxide LND treatment" with
-- ethylene-oxide treatment --.

Signed and Sealed this

Sixth Day of June, 2000

Attest:

Q. TODD DICKINSON

*Attesting Officer*  *Director of Patents and Trademarks*